United States Patent
Westwood et al.

Patent Number: 4,510,143
Date of Patent: Apr. 9, 1985

[54] ANTIALLERGIC PYRIMIDO[1,2-A]QUINOXALIN-2-CARBOXYLIC ACID DERIVATIVES

[75] Inventors: Robert Westwood, Faringdon; Peter Miller; Ian R. Ager, both of Swindon; David P. Kay, Purton, all of England

[73] Assignee: Roussel Uclaf, Paris, France

[21] Appl. No.: 465,669

[22] Filed: Feb. 10, 1983

[30] Foreign Application Priority Data

Feb. 17, 1982 [GB] United Kingdom ............... 8204634

[51] Int. Cl.³ .................. A61K 31/505; C07D 487/04
[52] U.S. Cl. ................................. 514/250; 544/250
[58] Field of Search ................. 544/250; 424/251

[56] References Cited

U.S. PATENT DOCUMENTS

| | | | |
|---|---|---|---|
| 3,887,566 | 6/1975 | Rodway et al. | 546/70 |
| 4,017,625 | 4/1977 | Kadin | 424/251 |
| 4,066,766 | 1/1978 | Kadin | 424/251 |
| 4,145,419 | 3/1979 | Rowlands et al. | 424/248.4 |
| 4,151,280 | 4/1979 | Rowlands et al. | 424/250 |
| 4,207,318 | 6/1980 | Rowlands et al. | 424/248.4 |
| 4,223,031 | 9/1980 | Covington et al. | 424/251 |
| 4,254,123 | 3/1981 | Ramm et al. | 424/250 |
| 4,279,912 | 7/1981 | Ager et al. | 424/258 |
| 4,291,033 | 9/1981 | Barnes et al. | 424/250 |
| 4,333,934 | 6/1982 | Barnes et al. | 424/250 |

FOREIGN PATENT DOCUMENTS 0080941 6/1983 European Pat. Off. .

OTHER PUBLICATIONS

Hermecz et al., J. Chem. Soc. Perkin Transactions I, 1977 (7), pp. 789–795.

Golankiewicz, Chemical Abstracts, vol. 62, 1659h–1660c (1965).
Otsumasu et al., Chemical Abtracts, vol. 81, 91574b (1974).

Primary Examiner—Donald G. Daus
Assistant Examiner—Diana G. Rivers
Attorney, Agent, or Firm—Charles A. Muserlian

[57] ABSTRACT

Novel pyrimidines of the formula

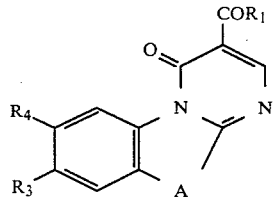

wherein $R_1$ is selected from the group consisting of —OH, cation of metals and organic bases, alkoxy of 1 to 5 carbon atoms, hydrazino and 1H-tetrazol-5-yl-amino, A is selected from the group consisting of

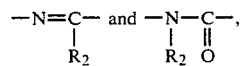

$R_2$ is selected from the group consisting of hydrogen and alkyl of 1 to 5 carbon atoms and $R_3$ and $R_4$ are individually selected from the group consisting of hydrogen, halogen and alkyl and alkoxy of 1 to 5 carbon atoms with the proviso that when $R_1$ is alkoxy of 1 to 5 carbon atoms, $R_2$ is not hydrogen and their non-toxic, pharmaceutically acceptable acid addition salts having anti-allergic properties.

18 Claims, No Drawings

ANTIALLERGIC PYRIMIDO[1,2-A]QUINOXALIN-2-CARBOXYLIC ACID DERIVATIVES

STATE OF THE ART

Commonly assigned U.S. patent application Ser. No. 444,040 filed Nov. 23, 1982 and U.S. Pat. Nos. 4,333,934 and 4,254,123 and to a lesser degree U.S. Pat. Nos. 4,145,419, 4,279,912, 4,151,280, 4,207,318 and 4,291,033 describe tricyclic compounds having antiallergic activity but with a different chemical structure. Also pertinent is J. Chem. Soc., Perkin I (1977), p. 789.

OBJECTS OF THE INVENTION

It is an object of the invention to provide the novel pyrimidines of formula I and their non-toxic, pharmaceutically acceptable acid addition salts and their preparation and novel intermediates.

It is another object of the invention to provide novel antiallergic compositions and to a method of combatting allergies in warm-blooded animals.

These and other objects and advantages of the invention will become obvious from the following detailed description.

THE INVENTION

The novel compounds of the invention are selected from the group consisting of pyrimidines of the formula wherein $R_1$ is selected from the group consisting of —OH, cation of metals and organic bases, alkoxy of 1 to 5 carbon atoms, hydrazino and 1H-tetrazol-5-yl-amino, A is selected from the grou consisting of $$-N=C- \text{ and } -N-C-,$$
$$\phantom{-N=}\underset{R_2}{|} \phantom{\text{ and } -N}\underset{R_2}{|}\underset{O}{\|}$$

$R_2$ is selected from the group consisting of hydrogen and alkyl of 1 to 5 carbon atoms and $R_3$ and $R_4$ are individually selected from the group consisting of hydrogen, halogen and alkyl or alkoxy of 1 to 5 carbon atoms with the proviso that when $R_1$ is alkoxy of 1 to 5 carbon atoms, $R_2$ is not hydrogen and their non-toxic, pharmaceutically acceptable acid addition salts.

Examples of $R_1$, $R_3$ and $R_4$ as alkoxy are methoxy, ethoxy, propoxy, isopropoxy and butoxy. Examples of $R_2$ as alkyl are methyl, ethyl and propyl and examples of $R_3$ and $R_4$ as halogen are fluorine, chlorine and bromine.

When $R_1$ is other than —OH, the compounds of formula I are basic in nature and may form acid addition salts with inorganic acids such as hydrochloric acid, hydrobromic acid, hydroiodic acid, nitric acid, sulfuric acid or phosphoric acid or organic acids such as acetic acid, formic acid, benzoic acid, oxalic acid, glyoxylic acid and aspartic acid or alkanesulfonic acids such as methanesulfonic acid or arylsulfonic acids such as benzenesulfonic acid.

The compounds of formula I wherein $R_1$ is hydroxyl can form metal salts and salts with nitrogenous bases. Thus, for example, metal salts which may be formed include alkali metal salts such as sodium, potassium and lithium salts and alkaline earth metal salts such as calcium salts as well as aluminum and magnesium salts. Salts which may be formed with nitrogenous bases include, for example, salts formed with ammonia and amines such as tromethamine, lysine, arginine and triethanolamine.

Among the preferred compounds of formula I are those wherein $R_3$ and $R_4$ are individually hydrogen or chlorine or methyl or methoxy and those wherein $R_2$ is hydrogen or methyl and their non-toxic, pharmaceutically acceptable acid addition salts. Especially preferred are 1-oxo-1H-pyrimido[1,2-a]quinoxalin-2-carboxylic acid, N-(5-tetrazolyl)-1-oxo-1H-pyrimido[1,2-a]quinoxalin-2-carboxamide and 1,5-dioxo-1,6-dihydropyrimido[1,2-a]quinoxalin-2-carboxylic acid and their acid addition salts and salts.

The novel process of the invention for the preparation of compounds of formula I wherein $R_1$ is —OH comprises cyclizing a compound of the formula wherein A, $R_3$ and $R_4$ have the above definitions. Cyclization can be effected by heating preferably at reflux temperatures for one to five hours.

The process of the invention for the preparation of the compounds of formula I wherein $R_1$ is alkoxy, hydrazino or 1H-tetrazol-5-yl-amino comprises reacting the free acid of formula I wherein $R_1$ is —OH or reactive derivative thereof with a compound of the formula $$R_1'-H \qquad\qquad III$$

wherein $R_1'$ is alkoxy of 1 to 5 carbon atoms, hydrazino or 1H-tetrazol-5-yl-amino.

Reactive derivatives of the acid of formula I which may be employed include, for example, the acid anhydride, mixed anhydrides, esters and acid halides, particularly preferred being the use of the acid chloride. Such reactive derivatives may be prepared by conventional methods optionally in situ in the reaction mixture. When an acid of formula I is employed per se, then it is generally advantageous to carry out the reaction in the presence of an acid activating and/or dehydrating agent such as carbonyldiimidazole. The reaction is conveniently carried out in the presence of a solvent such as dimethylformamide.

The compounds of formula I wherein $R_1$ is alkoxy may also be prepared by cyclization of a compound of the formula

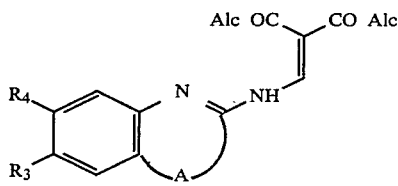

wherein A, R₃ and R₄ are as hereinbefore defined and Alc is alkoxy of 1 to 5 carbon atoms. Cyclization is conveniently effected by heating or using a condensing agent such as polyphosphoric acid.

The compounds of formula I may be converted into their salts by methods well known in the art. Thus compounds of formula I wherein $R_1$ is other than —OH may, if desired, be reacted with an acid while compounds of formula I wherein $R_1$ is —OH may, if desired, be reacted with a base.

The compounds of formula II, useful as starting materials in the process above are novel compounds constituting a further feature of the invention. They may for example be obtained by reaction of a compound of the formula

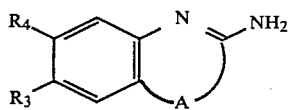

wherein A, R₃ and R₄ are as hereinbefore defined with a compound of the formula

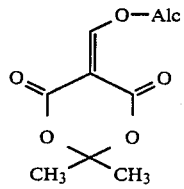

wherein Alc has the above meaning. The reaction is preferably effected in the presence of an organic solvent such as methanol.

The compounds of formula IV, useful as starting materials in the process may also be obtained from compounds of formula V by reaction with a di-alkyl ethoxymethylenemalonate of 1 to 5 alkyl carbon atoms, preferably in the presence of an organic solvent such an xylene.

The novel antiallergic compositions of the invention and comprised of an antiallergically effective amount of at least one compound of formula I and its non-toxic, pharmaceutically acceptable acid addition salts and a pharmaceutical carrier or excipient. The compositions may be in the form of tablets, dragees, gelatin capsules, granules, suppositories, syrups, aerosols, creams, ointments and injectable suspensions and/or solutions.

Examples of suitable excipients are talc, arabic gum, lactose, starch, magnesium stearate, cocoa butter, aqueous or non-aqueous vehicles, fatty substances of an animal or vegetable origin, paraffin derivatives, glycols, various wetting, dispersing or emulsifying agents and-/or preservatives.

Advantageously the compositions may be formulated as dosage units, each unit being adapted to supply a fixed dose of active ingredient. Suitable dosage units for adults contain from 0.1 mg to 1000 mg, preferably from 1 mg to 100 mg of active ingredient. The oral daily dosage, which may be varied according to the compound used, the subject treated and the complaint concerned, may, for example, be from 0.25 to 100 mg per day in adults.

The compositions due to their antiallergic activity are useful for the treatment of allergic asthma and asthmatic bronchitis of allergic origin.

The novel method of the invention for combatting allergic symptoms in warm-blooded animals, including humans, comprises administering to warm-blooded animals an antiallergically effective amount of at least one compound of formula I and their non-toxic, pharmaceutically acceptable acid addition salts. The compounds may be administered orally, rectally, locally or parenterally and the usual daily dose is 0.003 to 1.5 mg/kg depending on the compound used and the condition treated.

In the following examples there are described several preferred embodiments to illustrate the invention. However, it is to be understood that the invention is not intended to be limited to the specific embodiments.

EXAMPLE 1

1-Oxo-1H-pyrimido[1,2-a]quinoxaline-2-carboxylic acid

STEP A:
N-(2'-quinoxalinyl)-aminomethylene-isopropylidene malonate

A solution of 2.0 g of methoxymethylene-isopropylidene malonate in 40 ml of methanol was added to a solution of 2.0 g of 2-aminoquinoxaline in 40 ml of methanol and a white precipitate formed which was filtered off and washed with methanol to obtain 2.8 g of N-(2'-quinoxalinyl)-aminomethylene-isopropylidene malonate (68% yield).

STEP B:
1-oxo-1H-pyrimido[1,2-a]quinoxaline-2-carboxylic acid 1.6 g of N-(2'-quinoxalinyl)-aminomethylene-isopropylidene malonate were dissolved in 50 ml of dichloromethane and 50 ml of polyphosphoric acid were added thereto. The mixture obtained was formed in an open flask over a steam bath at 60° C. to remove solvent and then was heated at 60° C. for a further hour to complete the reaction. After cooling, the resultant solution was diluted with water and the precipitate obtained was filtered off, washed with water and recrystallized from chloroform-methanol to obtain 1.21 g (92% yield) of 1-oxo-1H-pyrimido[1,2-a]quinoxaline-2-carboxylic acid melting at 216°–8° C.

EXAMPLE 2

N-(5-Tetrazolyl)-1-oxo-1H-pyrimido[1,2-a]quinoxaline-2-carboxamide

A mixture of 250 mg of 1-oxo-1H-pyrimido[1,2-a]quinoxaline-2-carboxylic acid and 200 mg of carbonyldiimidazole in 5 ml of dry dimethylformamide was heated over a steam bath for 15 minutes and then 100 mg of 5-aminotetrazole were added thereto. The mixture obtained was heated over a steam bath for another 30 minutes and was then poured into water and left at room temperature for 1 hour. The solid obtained was filtered off, was washed with water and ether and dried to obtain 240 mg (61% yield) of N-(5-tetrazolyl)-

1-oxo-1H-pyrimido[1,2-a]quinoxaline-2-carboxamide melting above 300°.

EXAMPLES 3 to 10

(a) Using a method similar to that of Example 1 but starting from the corresponding compound of formula V in which A, $R_2$, $R_3$ and $R_4$ have the meanings indicated in Table II, the products of Examples 3, 4, 6, 7, 8 and 10 were prepared (see Table II below).

(b) Using a method similar to that of Example I in which A, $R_3$ and $R_4$ have the meanings indicated in Table II, the products of Examples 5 and 9 were prepared (see Table II below).

EXAMPLE 11

1,5-Dioxo-1,6-dihydropyrimido[1,2-a]quinoxaline-2-carbohydrazide

A mixture of 500 mg of 1,5-dioxo-1,6-dihydropyrimido[1,2-a]-quinoxalin-2-carboxylic acid and 400 mg of carbonyldiimidazole in 20 ml of dimethylformamide was warmed over a steam bath for 15 minutes and then was cooled in an ice-bath and treated with 1.0 ml of a solution in dimethylformamide containing 1.1 g/10 ml of hydrazine hydrate overnight. The resultant mixture was filtered to obtain 500 mg (95% yield) of 1,5-dioxo-1,6-dihydropyrimido[1,2-a]quinoxaline-2-carbohydrazide melting at >300° C.

starch, talc, magnesium stearate q.s. for one tablet with a final weight of 100 mg.

EXAMPLE 13

A dosedaerosol was prepared delivering per dose 2 mg of the product of Example 8, 0.15 mg of an emulsifier and 50 mg of propellant.

PHARMACOLOGICAL ACTIVITY

Passive cutaneous anaphylaxis in the rat (PCR)

Passive cutaneous anaphylaxis in the rat was carried out in male Wistar rats weighing 180–200 g which were sensitized by intradermal injection into four sites on shaved backs to produce a passive cutaneous reaction mediated by Ig G antibodies (a 4 hour sensitization following injection of antiserum heated at 56° C. for one hour). Antigen challenge was carried out in the same way with 1 mg of ovalbumen together with 0.5 ml of 1% Evans blue dye solution being injected intravenously and 30 minutes later, the animals were killed and the severity and area of each blue spot was scored when viewed from the reverse side of the skin. The inhibition observed following oral administration of the tested compounds is given in Table I.

TABLE I

| Product of | % inhibition of Ig G PCR | | |
|---|---|---|---|
| Example | 0.1 mg/kg | 1 mg/kg | 10 mg/kg |
| 1 | | 9.9 | 50.3 |
| 2 | | 29.9 | 48.6 |

TABLE II

| EXAMPLE | $R_1$ | A | $R_2$ | $R_3$ | $R_4$ | M. pt. | Formula | Analysis Calc. C | H | N | Analysis Found C | H | N |
|---|---|---|---|---|---|---|---|---|---|---|---|---|---|
| 1 | OH | N=<$R_2$ | H | H | H | 225–8° | $C_{12}H_7N_3O_3$ | 59.76 | 2.93 | 17.42 | 59.49 | 3.12 | 17.55 |
| 2 | NH—<(N—N / N—N H) | " | H | H | H | >300° | $C_{13}H_8N_8O_2C_3H_4N_2$* | 51.06 | 3.22 | 37.22 | 50.98 | 3.34 | 37.19 |
| 3 | OH | " | Me | Me | Me | 240–3° | $C_{15}H_{13}N_3O_3$ | 63.60 | 4.63 | 14.83 | 63.32 | 4.65 | 14.79 |
| 4 | OH | " | H | Me | Me | 227–30 | $C_{14}H_{11}N_3O_3$ | 62.45 | 4.12 | 15.61 | 62.20 | 4.16 | 15.67 |
| 5 | NH—<(N—N / N—N H) | " | H | Me | Me | >270° | $C_{15}H_{12}N_8O_2$ | 53.57 | 3.60 | 33.32 | 53.32 | 3.65 | 33.12 |
| 6 | OH | " | H | H | OMe | 235–7° | $C_{13}H_9N_3O_4$ | 57.57 | 3.34 | 15.49 | 57.42 | 3.41 | 15.59 |
| 7 | OH | " | H | Cl | Cl | 237–40 | $C_{12}H_5N_3O_3Cl_2\cdot\frac{1}{4}H_2O$ | 45.81 | 1.76 | 13.35 | 45.95 | 1.74 | 13.42 |
| 8 | OH | N—C / \| \|\| $R_2$ O | H | H | H | >300° | $C_{12}H_7N_3O_4$ | 56.04 | 2.74 | 16.34 | 55.76 | 2.87 | 16.40 |
| 9 | NH—<(N—N / N—N H) | " | H | H | H | >300° | $C_{13}H_8N_8O_3$ | 48.15 | 2.48 | 34.56 | 48.36 | 3.24 | 34.93 |
| 10 | OH | " | Me | H | H | 216–8° | $C_{13}H_9N_3O_4$ | 57.57 | 3.34 | 15.49 | 57.31 | 3.44 | 15.57 |
| 11 | NHNH$_2$ | " | H | H | H | >300° | $C_{12}H_9N_5O_3$ | 53.14 | 3.34 | 25.82 | 52.27 | 3.34 | 25.89 |

*Contains 1 mole imidazole

EXAMPLE 12

Tablets were prepared containing 15 mg of the product of Example 8 and sufficient excipient of lactose, TABLE I-continued

| Product of Example | % inhibition of Ig G PCR | | |
|---|---|---|---|
| | 0.1 mg/kg | 1 mg/kg | 10 mg/kg |
| 8 | 40.5 | 52.4 | 94.1 |
| 9 | 19 | 23 | 35 |
| 10 | | 15.6 | 20.5 |

Various modifications of the products and processes of the invention may be made without departing from the spirit or scope thereof and it should be understood that the invention is intended to be limited only as defined in the appended claims.

What we claim is:

1. A compound selected from the group consisting of the formula

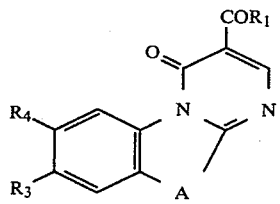

wherein $R_1$ is selected from the group consisting of —OH, non-toxic, pharmaceutically acceptable cation of metals and organic bases, alkoxy of 1 to 5 carbon atoms, hydrazino and 1H-tetrazol-5-yl-amino, A is selected from the group consisting of

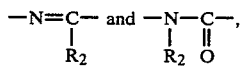

$R_2$ is selected from the group consisting of hydrogen and alkyl of 1 to 5 carbon atoms and $R_3$ and $R_4$ are individually selected from the group consisting of hydrogen, halogen and alkyl or alkoxy of 1 to 5 carbon atoms with the proviso that when $R_1$ is alkoxy of 1 to 5 carbon atoms, $R_2$ is not hydrogen and their non-toxic, pharmaceutically acceptable acid addition salts.

2. A compound of claim 1 wherein $R_3$ and $R_4$ are inividually selected from the group consisting of hydrogen, chlorine, methyl and methoxy.

3. A compound of claim 1 wherein $R_2$ is hydrogen or methyl.

4. A compound of claim 1 selected from the group consisting of 1-oxo-1H-pyrimido[1,2-a]quinoxalin-2-carboxylic acid and salts thereof and its non-toxic, pharmaceutically acceptable acid addition salts.

5. A compound of claim 1 selected from the group consisting of N-(5-tetrazolyl)-1-oxo-1H-pyrimido[1,2-a]quinoxalin-2-carboxamide and its non-toxic, pharmaceutically acceptable acid addition salts.

6. A compound of claim 1 selected from the group consisting of 1,5-dioxo-1,6-dihydro-pyrimido[1,2-a]quinoxalin-2-carboxylic acid and salts thereof and its non-toxic, pharmaceutically acceptable acid addition salts.

7. An antiallergic composition comprising an antiallergically effective amount of at least one compound of claim 1 and a pharmaceutical carrier.

8. A composition of claim 7 wherein $R_3$ and $R_4$ are individually selected from the group consisting of hydrogen, chlorine, methyl and methoxy.

9. A composition of claim 7 wherein $R_2$ is hydrogen or methyl.

10. A composition of claim 7 wherein the active compound is selected from the group consisting of 1-oxo-1H-pyrimido[1,2-a]quinoxalin-2-carboxylic acid and salts thereof and its non-toxic, pharmaceutically acceptable acid addition salts.

11. A composition of claim 7 wherein the active compound is selected from the group consisting of N-(5-tetrazolyl)-1-oxo-1H-pyrimido[1,2-a]quinoxalin-2-carboxamide and its non-toxic, pharmaceutically acceptable acid addition salts.

12. A composition of claim 7 wherein the active compound is selected from the group consisting of 1,5-dioxo-1,6-dihydro-pyrimido[1,2-a]quinoxalin-2-carboxylic acid and salts thereof and its non-toxic, pharmaceutically acceptable acid addition salts.

13. A method of treating allergic symptoms in warm-blooded animals comprising administering to warm-blooded animals an antiallergically effective aamount of at least one compound of claim 1.

14. A method of claim 13 wherein $R_3$ and $R_4$ are individually selected from the group consisting of hydrogen, chlorine, methyl and methoxy.

15. A method of claim 13 wherein $R_2$ is hydrogen or methyl.

16. A method of claim 13 wherein the active compound is selected from the group consisting of 1-oxo-1H-pyrimido[1,2-a]quinoxalin-2-carboxylic acid and salts thereof and its non-toxic, pharmaceutically acceptable acid addition salts.

17. A method of claim 13 wherein the active compound is selected from the group consisting of N-(5-tetrazolyl)-1-oxo-1H-pyrimido[1,2-a]quinoxalin-2-carboxamide and its non-toxic, pharmaceutically acceptable acid addition salts.

18. A method of claim 13 wherein the active compound is selected from the group consisting of 1,5-dioxo-1,6-dihydro-pyrimido[1,2-a]quinoxalin-2-carboxylic acid and salts thereof and its non-toxic, pharmaceutically acceptable acid addition salts.

* * * * *